(12) United States Patent
Benz

(10) Patent No.: US 6,308,584 B1
(45) Date of Patent: Oct. 30, 2001

(54) PROCESS, CARTRIDGE AND DEVICE FOR INTRODUCING A PARTICULATE MATERIAL INTO A LIQUID

(75) Inventor: Rolf Martin Benz, Allschwil (CH)

(73) Assignee: Sotax AG, Allschwil (CH)

( * ) Notice: Subject to any disclaimer, the term of this patent is extended or adjusted under 35 U.S.C. 154(b) by 0 days.

(21) Appl. No.: 09/569,290

(22) Filed: May 11, 2000

(30) Foreign Application Priority Data

May 11, 1999 (CH) .................................................. 0892/99

(51) Int. Cl.[7] .................................................. G01N 33/00
(52) U.S. Cl. .................................................. 73/866
(58) Field of Search ............................... 73/866; 206/219, 206/221, 568; 220/260, 281

Primary Examiner—Robert Raevis
(74) Attorney, Agent, or Firm—Sidley Austin Brown & Wood, LLP

(57) ABSTRACT

The invention relates to a process for introducing a particulate material, for example pellets, granules or powder, into a liquid, and a cartridge and a device for carrying out this process. The material is introduced into a cartridge having a sleeve, an axis and a base arranged in the interior of the sleeve and displaceable along the axis away from a stop. Thereafter, the cartridge, in a position in which its axis is approximately perpendicular and the base rests against the stop under its own weight, is allowed to fall into the liquid, the cartridge being guided by a guide tube. On immersion in the liquid, the base is displaced upward away from the stop by the liquid, with the result that the material is ejected at least for the most part from the cartridge.

5 Claims, 3 Drawing Sheets

Figure 1:
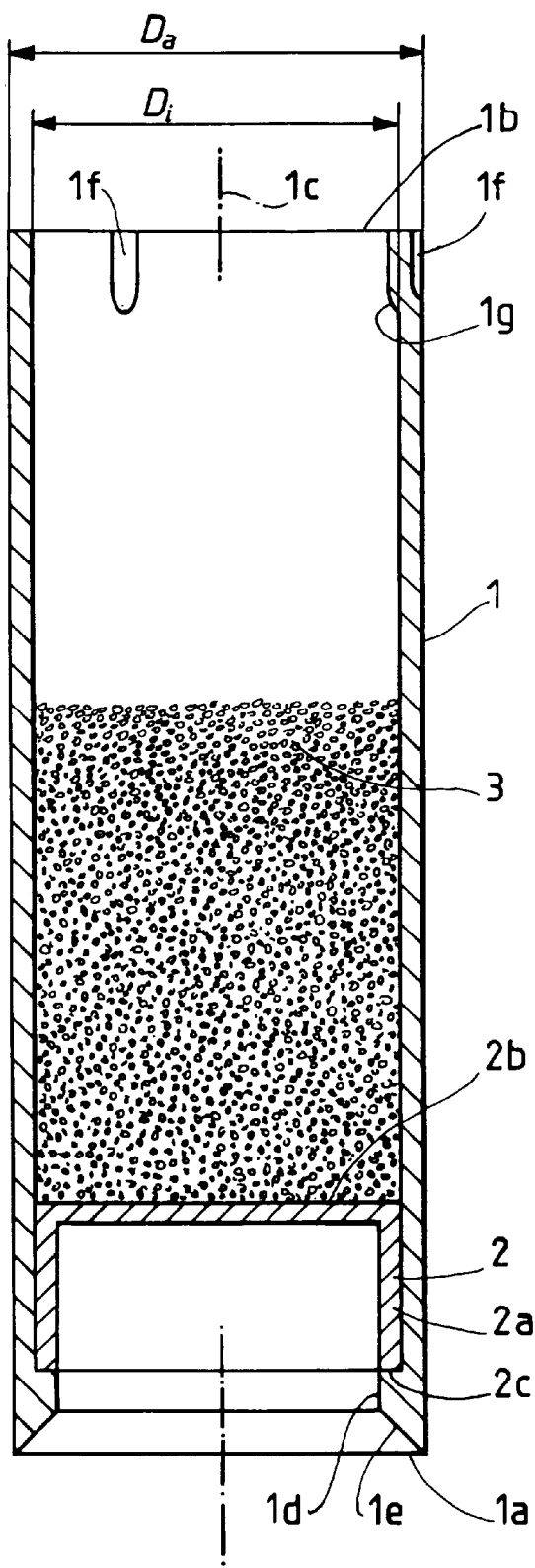

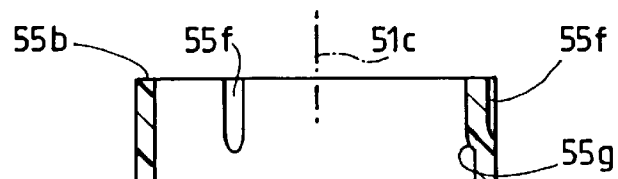
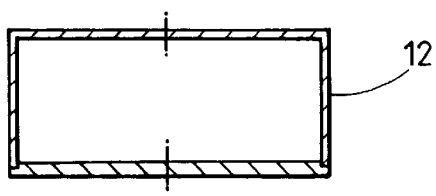
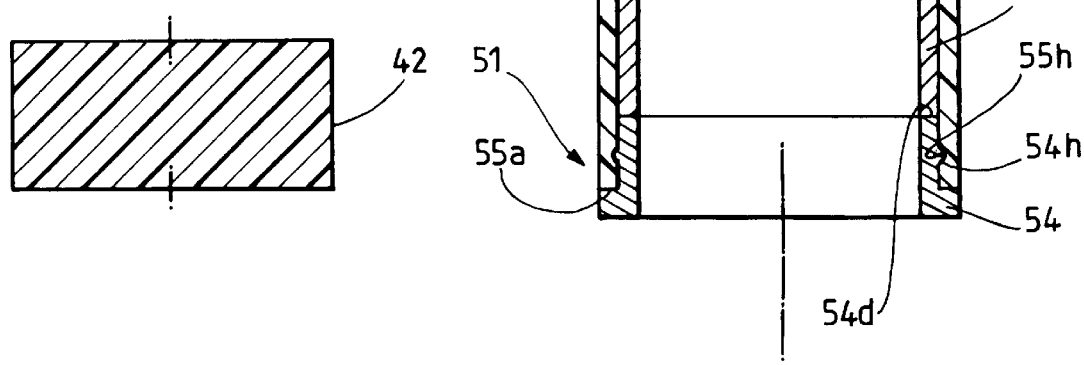

PROCESS, CARTRIDGE AND DEVICE FOR INTRODUCING A PARTICULATE MATERIAL INTO A LIQUID

BACKGROUND OF THE INVENTION

The invention relates to a process for introducing a particulate material, for example pellets, granules or powder into a liquid.

In the development and in particular in the routine quality control of solid drug forms, the determination of the active substance dissolution rate in the dissolution process of a drug is of great importance. For this reason, the national pharmacopeias and the European Pharmacopoeia contain exact specifications regarding the instrument parameters of the tester as well as regarding the test procedure. Of primary importance in this regard is the United States Pharmacopeia (USP). Every dissolution tester must comply with the USP specifications. Regular inspections by the health authorities, such as, for example, the Food and Drug Administration (FDA) of the USA, stringently check for compliance with the specifications.

According to the USP specifications, the determination of the active substance dissolution is performed simultaneously with six test specimens, which are introduced in each case into a test vessel containing simulated gastric or intestinal fluid. The dissolution process takes place, for example, at 37 degrees Celsius, the dissolution medium being stirred by means of a standardized stirrer at a specified speed. In many cases, these tests are carried out with tablets or capsules.

SUMMARY OF THE INVENTION

A problem is encountered when carrying out such a test with the use of, for example, medicaments which are administered as fine particulate material, for example in the form of pellets, in capsules. Pellets are approximately spherical particles which typically have a diameter of 0.4 to 1.2 mm. Owing to their size and their composition, they tend to be readily electrostatically chargeable. If the pellets must be introduced automatically, for example through a metal tube, into the liquid, they therefore tend to adhere to the tube wall. Moreover, owing to the service tension of the liquid, they tend to remain on its surface and not to become immersed in the liquid. An important problem is also the wettability of the pellets, powder or granules. However, the wettability of the material to be tested is an important precondition for the reproducible test. For these reasons, in dissolution tests to date, pellets have frequently been weighed on a spoon and stirred into the liquid with said spoon manually, whereupon the spoon has to be cleaned again. The process is of course therefore considerably timeconsuming and expensive.

It is therefore the object of the present invention to provide a process which permits the manual, semiautomatic or automatic introduction of fine particulate material, for example of pellets, of granules or of powder, into a liquid, so that the dosage can be checked with sufficient accuracy, the total intended amount can be introduced as far as possible simultaneously, at a defined time, into the liquid and at the same time good distribution and hence as good wetting of the material as possible in the liquid are ensured.

This object is achieved by a process for introducing a particulate material into a liquid, wherein the material is introduced into a cartridge having a sleeve, an axis and a base arranged in the interior of the sleeve and displaceable along the axis away from a stop, and wherein the cartridge, in a position in which its axis is approximately perpendicular and the base, as a result of its weight, rests against the stop, is allowed to fall into the liquid, so that the base is displaced by the liquid upward away from the stop and at least the major part of the material is ejected from the cartridge.

The present invention also relates to a cartridge for carrying out the process, wherein the cartridge has a sleeve with an axis and a stop and a base arranged displaceably in the sleeve and resting against the stop as a result of its own weight in one position of the cartridge.

The invention furthermore relates to a device for carrying out the abovementioned process, which comprises at least one cartridge of the type defined above and at least one guide tube with a perpendicular axis and a lower open end for guiding a cartridge falling into a container coordinated with a guide tube and containing liquid.

The process according to the invention, the cartridge according to the invention and the device according to the invention have different advantages compared with the prior art. Thus, the invention has the advantage that exactly a specified amount of particulate material can be easily introduced into the liquid, even in the case of a small particle size, without particles remaining adhering to any part of the device outside the liquid or remaining on the surface of the liquid. The process according to the invention, the cartridge and the device are therefore particularly suitable for use in an automatic or semiautomatic solubility test, for example in quality controls. Process, cartridge and device are also especially suitable for introducing particulate materials comprising very small particles into a liquid, i.e. materials comprising particles having a particle size of usually not more than 1.2 mm and generally at least 0.4 mm or comprising even smaller particles.

DETAILED DESCRIPTION OF THE PREFERRED EMBODIMENTS

Figure 2:
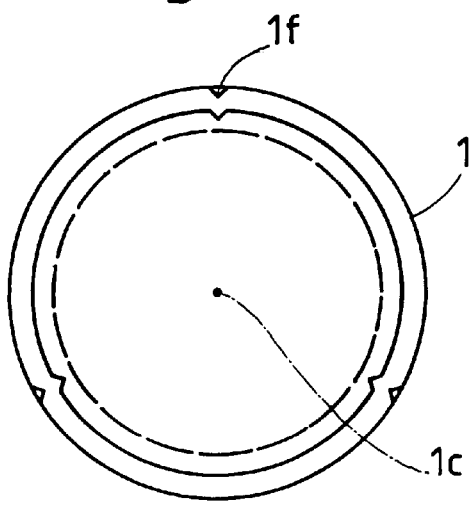
Figure 3:
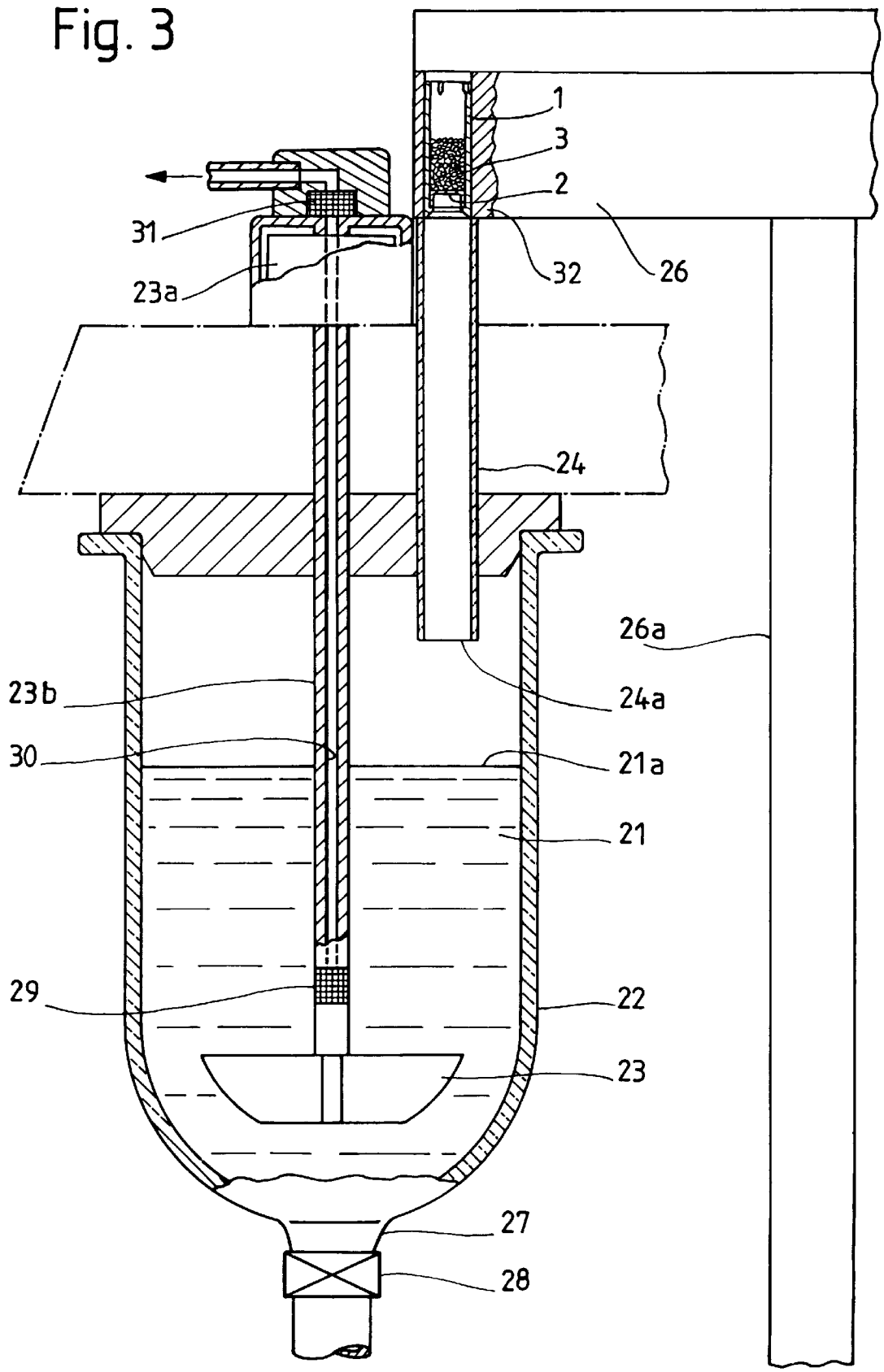

Below, embodiments of the invention are described with reference to a drawing. In the drawing, FIG. 1 shows an axial section of a cartridge for carrying out the process according to the invention, FIG. 2 shows a view of this cartridge from above, FIG. 3 shows a partial section through a highly schematic device for carrying out the process, FIG. 4 shows a variant of the base of the cartridge, FIG. 5 shows a further variant of the base of the cartridge and FIG. 6 shows an axial section of another embodiment of the cartridge.

A cartridge for carrying out the process according to the invention consists of an essentially cylindrical sleeve 1 having two ends 1a and 1b and a base 2 displaceable in the sleeve 1. Both sleeve 1 and base 2 consist of a material resistant to the liquid, for example of stainless steel. The sleeve 1 is in the form of a hollow cylinder with an external diameter $D_a$ and an internal diameter $D_i$ and has an axis 1c. Close to the lower end 1a, it has a constriction serving as a stop 1d, it being possible for the inner surface on the lower side of the constriction also to have, for example, a conical section 1e widening toward the lower end 1a of the sleeve 1. The other end of the sleeve is provided, for example, with three notch-like creases 1f which are parallel to the axis 1c and together form securing stop 1g. The base 2 is present inside the sleeve 1. In the example shown in FIG. 1, the base is beaker-shaped, i.e. it consists of a short hollow cylindrical wall 2a and a plate-like, approximately flat section 2b. The base is inserted into the sleeve and displaceably guided in the latter with a small play, so that it can slide with only minimum friction along the axis $1c$, between the stop $1d$ and the securing stop $1g$, and no particles of the particulate material 3 introduced into the cartridge can fall down between the sleeve 1 and the base 2. In the upright position, which is referred to below as the normal position and in which the axis $1c$ of the sleeve 1 is perpendicular and the base 2, as a result of its weight, is at the bottom, the edge $2c$ of the wall $2b$ rests on the stop $1d$.

Next, a device for carrying out automated dissolution tests will be briefly described. Such a device has a plurality of automatically refillable and cleanable liquid containers 22, for example seven thereof. These containers can be filled with the desired liquid 21, for example with simulated gastric or intestinal fluid. Dissolution tests can then be carried out simultaneously in all containers 22, except for one. The liquid 21 in the remaining container 22 serves as a reference. Each container 22 is provided with a suitable stirring device corresponding to the standards, i.e. for example with a paddle 23 having a motor drive $23a$. For each container 22 in which the dissolution test is to be carried out, the device has a guide tube 24 through which a cartridge can be allowed to fall on the liquid surface $21a$. Each guide tube 24 has an internal diameter which is slightly greater than the external diameter $D_a$ of a cartridge and a length which is at least equal to, and, for example, one to eight times the length of a cartridge. Each guide tube 24 is mounted above the liquid container coordinated with it and projects, for example, from above slightly into said container and does so in such a way that the axis of the guide tube is perpendicular and that one end $24a$ of the guide tube is, for example, at least half the cartridge length and at most four cartridge lengths above the plane in which the liquid surface $21a$ comes to rest in the operating state. In addition, the device has a feed means 26 shown merely schematically in FIG. 3. Said feed means may have, for example, a magazine 32 with a suitable number of cartridges, for example a magazine with 6 rows of 10 cartridges each. A guide tube is coordinated with each row, a cartridge from each row simultaneously being allowed to fall through the guide tube 24 coordinated with the row into the coordinated liquid container 22 at the start of a dissolution test. The magazine 32 is moved in each case at the desired time so that cartridges present in it are pushed via the guide tube 24 and consequently fall through it into the liquid 21. The means 26 and hence also the guide tube are held by a support $26a$ likewise shown only schematically in FIG. 3.

The device furthermore has means and apparatuses for thermostating the liquid containers 22 and for taking samples from the containers 22 at intervals. For this purpose, for example, the liquid 21 can be fed through a prefilter 29, a tube 30 running through the stirrer shaft $23b$ of the paddle 23 and a filter 31 to a measuring apparatus, where the dissolution of the test substances in the liquid 21 is analyzed, for example photometrically. However, it is also just as possible to introduce a separate, retractable tube from above into the liquid 21 and to carry out the sampling through this. To enable subsequent tests, too, to be carried out automatically, the device has a filling, emptying and cleaning system for the liquid containers 22 and a means for removing empty cartridges. In the embodiment shown, the emptying of the container 22 is effected through an outlet 27 with a closure 28, through which the cartridge too can be removed together with the liquid 21. Furthermore, the device preferably also has a control means which centrally controls the filling of the liquid containers 22, the supply of the material 3, the sampling, the measurements, the emptying and the cleaning of the containers 22, so that a large number of tests can be carried out automatically.

For introducing a particulate soluble material 3 to be tested, referred to below as test substance, into a liquid 21 serving as a test liquid, the sleeve is filled in a first step with an exactly measured amount of test substance 3, for example with a specified mass, such as, for example, 400 mg. The amount can be determined, for example, by weighing the cartridge and the material introduced into it or by weighing the material before introduction into the cartridge or possibly by a volumetric measurement. As shown in FIGS. 1 and 3, the cartridge can be filled if it is upright, i.e. in the normal position. The sleeve 1 together with the base 2 which rests sufficiently tightly against the inner surface of the sleeve 1, then serves as a vessel. In the next step, the filled cartridge as a whole is allowed to fall from the normal position onto the liquid surface $21a$. The cartridge is guided by a guide tube 24. As a result of the impact of the base and the resulting lifting forces on immersion of the cartridge in the liquid 21, the base 2 is then raised in the sleeve 1, moved as far as the securing stop $1g$ and secured by this to prevent it from leaving the sleeve 1. The test substance 3 is thus ejected. It has been found that the test substance 3 is for the most part ejected into the liquid 21 and, immediately after ejection, is enclosed on all sides by the liquid 21. Thus, at most a small part of the material remains on the liquid surface $21a$. The test substance 3 can therefore be introduced in a well defined, intended and reproducible manner into the liquid and then mixed with the liquid by means of the paddle. The cartridge subsequently sinks to the bottom of the liquid container 22 and remains lying there. Test substance residues which may remain in the cartridge rapidly come into contact with the liquid 21 and can subsequently also be dissolved.

The buoyancy which, after the impact of the cartridge on the liquid surface $21a$, results in the base 2 of the cartridge being raised and being moved as far as the securing stop $1g$ has various causes. On the one hand, it is of course generated by virtue of the fact that liquid is displaced by the penetration of the cartridge in which the base rests against the stop $1d$, against which act the gravitational force and, during rapid immersion, also the inertia of the liquid. On the other hand, however, the base 2 itself acts as a float since, on immersion of the cartridge, an air cushion remains under the beaker which is formed by the base 2.

Depending on the height from which the cartridge is allowed to fall onto the liquid surface $21a$, a further advantageous effect, which optimizes the ejection of the particulate material 3 from the cartridge, may be present. As a result of the inertia of the base 2 and of the material 3 filled into the cartridge and of the liquid 21, the air cushion which forms under the base 2 is briefly and temporarily compressed, with the result that the ejection takes place with a slight delay. The result of this is that the particulate material 3 is ejected for the most part only when the cartridge is fully immersed in the liquid 21, with the result that the fraction of pellets or granular or powder particles remaining on the surface is further reduced.

The process according to the invention, the cartridge according to the invention and the device according to the invention can also have designs other than those described above. FIG. 4 shows, for example, another embodiment of the base 12. The base 12 is a can which has a wall closed on all sides and comprising metallic material, for example stainless steel, and which is filled with air. A further variant is shown in FIG. 5. The base is a plastics body 42 comprising a light plastic which is resistant to the test liquid and/or coated with a metal film resistant to the test liquid, for example with a gold or aluminum film. What is important in these embodiments is that the density of the base as a whole is lower than that of the liquid 21, i.e. for example less than 1 g/cm³, so that the buoyancy of the base contributes to the upward displacement of the base in these embodiments too.

As shown in FIG. 6, the sleeve, too, can have a design other than the example shown in FIG. 1 and, for example, in particular need not be made of an integral body. The sleeve denoted as a whole by 51 in FIG. 6 is composed of a hollow cylinder 55 having a lower end 55a and an upper end 55b and an annular end piece 54 fastened to the lower end 55a of said cylinder. The hollow cylinder 55 can be made of, for example, a plastic and has creases 55f at the upper end 55b, as in the case of the embodiment shown in FIG. 1. Furthermore, the hollow cylinder 55 has an annular groove 55h in the vicinity of its lower end 55a. The end piece 54 is, for example, metallic and has an all-round bead 54h which, when the end piece 54 is mounted on the hollow cylinder 55, engages the annular groove 55h of the hollow cylinder. The bead 54h and the annular groove 55h together can form, for example, a catch, so that the end piece 54 can be pushed and thus clipped onto the hollow cylinder 55 during assembly. A base 2, which is of the same design as the base 2 shown in FIG. 1, is inserted into the sleeve 51. The base 2 is displaceable in the sleeve 51 along its axis 51c between a stop 54d and a securing stop 55g, the stop 54d being formed by the end piece 54 and the securing stop 55g by the creases 55f. It should also be mentioned here that there are of course other possibilities for mounting an end piece, which has or forms a stop, on a hollow cylinder. Thus, the hollow cylinder 55 may also have a bead, which then engages an annular groove in the end piece. The end piece can also be in the form of a thin sleeve which is pushed onto the outside of the hollow cylinder and has a stop projecting into the inside of the cylinder at the lower end 55a of said cylinder; in this case, the end piece will preferably have a bead which projects inward and engages an annular groove in the outside of the hollow cylinder. Furthermore, it is not necessary for the hollow cylinder 55 to be made of plastic and the end piece 54 of metal; the converse is just as possible, and it is of course also possible for both hollow cylinder 55 and end piece 54 to be made of metal and plastic, respectively.

Many other embodiments are also possible for the present invention. Thus, for example, it would be entirely possible for the sleeve 1 to have a form other than cylindrical, for example to be generally tetragonal in cross-section, with rounded corners. The base, too, need not necessarily be beaker-like or can-like but may, for example, also be in the form of a sphere. Furthermore, it is not absolutely essential for the sleeve 1 to have a securing stop 1g. It is in fact also entirely possible for the base 2 also to be ejected from the cartridge on immersion of the cartridge in the liquid 21. The base can then be inserted again subsequently. If the cartridge can be produced sufficiently economically, however, this variant is also suitable for using the cartridge as a disposable cartridge. Furthermore, it is not absolutely necessary for the device for introducing the particulate material 3 to have a guide tube 24; the cartridge can also be allowed to fall unguided from its normal position, automatically or manually, onto the liquid surface 21a.

The process according to the invention is incidentally by no means limited to applications for dissolution tests for pharmaceutical active substances in simulated gastric or intestinal fluid. It is also entirely possible to carry out dissolution tests with excipients. Dissolution tests in which the process according to the invention, the cartridge according to the invention and the device according to the invention can be used are however also carried out with foods, with colorants, with agrochemical products, etc., the liquid serving as solvent and its temperature of course being chosen in each case according to the problem.

What is claimed is:

1. A method of introducing a particulate material into a liquid, comprising the steps of introducing the material into a cartridge having a sleeve, a stop provided in an interior of the sleeve, and a base arranged in the interior of the sleeve and displaceable along a sleeve axis away from the stop; and dropping the cartridge, in a position in which the base, as a result of a weight of the material introduced into the cartridge and a base own weight, rests against the stop, into the liquid, whereby the base is displaced by the liquid upward away from the stop, and at least a major part of the material is ejected from the cartridge.

2. The method as claimed in claim 1, wherein the material introducing step comprises introducing the material into a cartridge all parts of which come into contact with the liquid after the cartridge falls into the liquid and which parts are formed of a material resistant to the liquid and insoluble therein upon the cartridge being left in the liquid at least for a certain time, whereby any material remaining in the cartridge is also dissolved, with the liquid being stirred after introduction of the cartridge.

3. The method as claimed in claim 1, comprising the step of guiding the cartridge in a vertical guide tube during its fall.

4. The method as claimed in claim 1, comprising the step of investigating, after introduction of the material into the liquid, a dissolution of the material therein.

5. The process as claimed in claim 1, comprising the step of arranging a plurality of cartridges in at least one row, with the cartridges being held in such a way that, as a result of a displacement step of the row, one individual cartridge in each case falls into a liquid-containing container associated with the row.

* * * * *